United States Patent [19]

Osborne et al.

[11] Patent Number: 5,004,610
[45] Date of Patent: Apr. 2, 1991

[54] SUBSATURATED NICOTINE TRANSDERMAL THERAPEUTIC SYSTEM

[75] Inventors: James L. Osborne, Mountain View; Melinda Nelson, Sunnyvale; David J. Enscore, Saratoga; Su I. Yum; Robert M. Gale, both of Los Altos, all of Calif.

[73] Assignee: ALZA Corporation, Palo Alto, Calif.

[21] Appl. No.: 537,672

[22] Filed: Jun. 14, 1990

Related U.S. Application Data

[63] Continuation-in-part of Ser. No. 206,546, Jun. 14, 1988, abandoned, and a continuation-in-part of Ser. No. 2,561, Jun. 13, 1989, abandoned.

[51] Int. Cl.$^5$ ............................................. A61F 13/02
[52] U.S. Cl. .................................... 424/448; 424/447
[58] Field of Search .............................. 424/448, 449

[56] References Cited

U.S. PATENT DOCUMENTS

| | | | |
|---|---|---|---|
| 3,252,802 | 5/1966 | Cunningham | 99/2 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,734,097 | 5/1973 | Zaffaroni | 128/268 |
| 3,742,951 | 7/1973 | Zaffaroni | 128/268 |
| 3,845,217 | 10/1974 | Ferno et al. | 426/3 |
| 3,870,794 | 3/1975 | Hutchinson et al. | 424/264 |
| 3,877,468 | 4/1975 | Lichtneckert et al. | 131/2 |
| 3,901,248 | 8/1975 | Lichneckert et al. | 131/2 |
| 3,926,188 | 12/1975 | Baker et al. | 128/260 |
| 3,996,245 | 12/1976 | Hartog et al. | 260/340.9 |
| 4,031,894 | 6/1977 | Urquhart et al. | 128/268 |
| 4,060,084 | 11/1977 | Chandrasekaran et al. | 128/260 |
| 4,125,623 | 11/1978 | Hartog et al. | 424/278 |
| 4,144,317 | 3/1979 | Higuchi et al. | 424/21 |
| 4,201,211 | 5/1980 | Chandrasekaran et al. | 128/268 |
| 4,379,454 | 4/1983 | Campbell et al. | 604/897 |
| 4,562,075 | 12/1985 | Rajadhyaksha | 514/788 |
| 4,573,995 | 3/1986 | Cheng et al. | 604/896 |
| 4,588,580 | 5/1986 | Gale et al. | 424/448 |
| 4,597,961 | 7/1986 | Enscore | 424/449 |
| 4,623,346 | 11/1986 | von Bittera et al. | 604/896 |
| 4,643,856 | 2/1987 | Nichols | 264/41 |

(List continued on next page.)

FOREIGN PATENT DOCUMENTS

| | | |
|---|---|---|
| 3438284 | 3/1985 | Denmark . |
| 0117027 | 8/1984 | European Pat. Off. . |
| 0273004 | 11/1987 | European Pat. Off. . |
| 0251425 | 1/1988 | European Pat. Off. . |
| 0305757 | 8/1988 | European Pat. Off. . |
| 61-251619 | 11/1986 | Japan . |
| 8702870 | 5/1987 | PCT Int'l Appl. . |
| 8801516 | 3/1988 | PCT Int'l Appl. . |
| 2171906 | 5/1990 | United Kingdom . |

OTHER PUBLICATIONS

S. H. Gelbach, W. A. Williams and J. I. Freeman, "Protective Clothing as a Means of Reducing Nicotine Absorption in Tobacco Harvesters," Archives of Environmental Health, pp. 111–114, Mar./Apr. 1979.
C. Carruthers and A. Neilson, "A Simplied Procedure for the Gas Chromatographic Determination of Nico-
(List continued on next page.)

Primary Examiner—Thurman K. Page
Assistant Examiner—Leon R. Horne
Attorney, Agent, or Firm—Steven F. Stone; Edward L. Mandell; Paul L. Sabatine

[57] ABSTRACT

Rate controlled transdermal nicotine delivery systems are disclosed which utilize an in-line adhesive to maintain the systems on the skin. The initial equilibrated concentration of nicotine in the nicotine reservoir and the adhesive is below saturation, preferably at a thermodynamic activity no greater than 0.50, and the reservoir comprises the nicotine dissolved in a material with respect to which the rate controlling element of the device is substantially impermeable. In preferred embodiments the initial loading of nicotine in the reservoir is sufficient to prevent the activity of the nicotine in the reservoir from decreasing by more than about 75% and preferably no more than about 25% during the predetermined period of administration; and the thickness of the adhesive, rate controlling membrane and reservoir layers are selected so that at least 50% and, preferably at least 75% of the initial equilibrated nicotine loading is in the reservoir layer.

29 Claims, 1 Drawing Sheet

U.S. PATENT DOCUMENTS

| | | | |
|---|---|---|---|
| 4,665,069 | 2/1987 | Rosenberg | 514/222 |
| 4,704,282 | 11/1987 | Campbell et al. | 424/449 |
| 4,715,387 | 5/1987 | Rose | 131/270 |
| 4,748,181 | 5/1988 | Hutchinson et al. | 514/343 |
| 4,758,434 | 7/1988 | Kydonieus et al. | 424/449 |
| 4,797,284 | 1/1989 | Lofer et al. | 424/449 |
| 4,839,174 | 6/1989 | Baker et al. | 424/447 |
| 4,920,989 | 5/1989 | Rose et al. | 131/270 |

OTHER PUBLICATIONS tine: Application of the Method to Mouse Skin," Mikrochimica Acta [Wein] 1980 II, pp. 59–66.

H. Schievelbein, "Nicotine, Resorption and Fate," Pharmac. Ther., vol. 18, pp. 233–248, 1982.

J. E. Rose, M. E. Jarvik and K. D. Rose, "Transdermal Administration of Nicotine," Drug and Alcohol Dependence, 13 (1984), pp. 209–213.

J. E. Rose, J. E. Herskovic, Y. Trilling and M. E. Jarvik, "Transdermal Nicotine Reduces Cigarette Craving and Nicotine Preference," Clin. Pharmacol Ther., pp. 450–456, Oct. 1985.

"Longterm Effects of Transdermal Nicotine Substitution in Behavioral Smoking Cessation," G. Buchkremer, et al., Abstracts, 6th World Conference on Smoking and Health, Nov. 9–12, Tokyo, Japan.

"Nicotine Replacement: The Role of Blood Nicotine Levels, Their Rate of Change, and Nicotine Tolerance," M. Russell, Nicotine Replacement: A Critical Evaluation, pp. 79–83 (1988).

SUBSATURATED NICOTINE TRANSDERMAL THERAPEUTIC SYSTEM

CROSS-REFERENCE TO RELATED PATENT APPLICATIONS

This application is a continuation-in-part of copending, coassigned application of Osborne. et al, Ser. No. 07/206,546 filed June 14, 1988, abandoned for Subsaturated Nicotine Transdermal Therapeutic System Having Improved Release Characteristics and a continuation-in-part of copending, coassigned PCT/US application Ser. No. 89/02561 of Osborne, et al, filed June 13, 1989, abandoned, for Subsaturated Transdermal Delivery Device. This application is related to the copending, coassigned patent application of Enscore, et al, Ser. No. 07/284,283 filed Dec. 14, 1988, which is a continuation-in-part of the application of Enscore, et al, for a Subsaturated Transdermal Therapeutic System Having Improved Release Characteristics, U.S. Ser. No. 06/906,730 filed Sept. 12, 1986, and now U.S. Pat. No. 4,908,027 dated Mar. 13, 1990, which is incorporated herein by reference. It is also related to copending, coassigned application of Wang, et al, for Polyisobutylene Adhesive For Transdermal Devices, filed Apr. 16, 1990, Ser. No. 07/509,644.

FIELD OF THE INVENTION

This invention relates to transdermal delivery systems for delivering nicotine through skin for an extended period of time and more particularly to such a system which utilizes a rate controlling membrane and an in-line adhesive. The device is used to assist a smoker to stop smoking.

BACKGROUND OF THE INVENTION

Transdermal devices for the delivery of a wide variety of biologically active agents have been known for some time and representative systems which utilize rate controlling membranes and in-line adhesives are disclosed in U.S. Pat. Nos. 3,598,122; 3,598,123; 3,742,951; 4,031,894, 4,144,317; 4,201,211 and 4,379,454 which are incorporated herein by reference. Such devices generally comprise an impermeable backing, a drug or active agent reservoir, a rate controlling membrane and a contact adhesive layer which can be laminated or heat sealed together to produce a transdermal delivery device.

It has also been proposed to deliver nicotine transdermally to aid in the cessation of smoking, see for example U.S. Pat. Nos. 4,597,961 and 4,839,174 which are incorporated herein by reference.

Although subsaturated systems are known, for example, U.S. Pat. Nos. 4,379,454 and 4,797,284, it is generally desirable that the agent reservoir comprise the agent to be delivered in a suitable carrier at a concentration above the saturation concentration in the carrier. This is done to maintain a unit activity source of the agent so that the delivery rate of the agent will remain substantially constant over the intended administration period, the amount of agent originally present over saturation being the depot or reservoir for the dose of agent ultimately delivered. If the concentration of the agent drops below unit activity during the delivery period, the rate of agent delivery will exhibit a corresponding decrease. It is also generally desirable to minimize the residual agent in the device after use. To accomplish this, devices normally utilize as a carrier, a material which has limited solubility for the agent to be delivered.

Although the devices of the prior art have been found useful for the delivery of a wide variety of agents, we have encountered significant problems in producing devices intended to deliver nicotine, an oily, liquid material having a high solubility in medically acceptable contact adhesives, at a substantially constant rate over the desired administration period.

As used herein, the expression "high nicotine solubility" as it relates to adhesives, is used to mean that nicotine is soluble in the adhesive to the extent that, at saturation, the adhesive layer is, (a) dissolved by nicotine; (b) becomes plasticized to the extent that it loses its cohesiveness or adhesiveness; or (c) contains concentrations of nicotine that produce adverse biological reactions when maintained in contact with the skin.

Regardless of the initial, as manufactured, concentration of active agent in the reservoir and other elements of typical prior art transdermal devices, such devices will equilibrate upon standing and the body contacting surface of the device will ultimately contain the agent at the same thermodynamic activity as the reservoir and other elements of device. Thus, when the agent is nicotine and even if the device is manufactured with a nicotine-free adhesive, we have observed that substantial quantities of nicotine will migrate from a saturated nicotine reservoir through the rate controlling membrane and into the adhesive layer prior to use.

As a result, a substantial amount of nicotine was found in the adhesive layer when applied to the skin which would be delivered through the skin in an uncontrolled manner before the rate controlling membrane exerted its effect on the nicotine remaining in the reservoir. Also, these high concentrations of nicotine in the adhesive layer and in direct contact with the skin may cause irritation or sensitization or produce undesirably high nicotine plasma levels during the initial period after application to the skin and prior to depletion of the initial loading of nicotine in the contact adhesive layer. In addition to the deleterious effects on the subject which may be caused by high concentrations of nicotine in the adhesive, most adhesives have their physical and adhesive properties degraded by such high concentrations of nicotine.

According to our invention, we have provided a rate controlled transdermal nicotine delivery device having an in-line adhesive. The device overcomes problems associated with delivering nicotine transdermally, which include irritation, sensitization and potential over dosage due to high concentrations of nicotine in the in-line adhesive and the adverse effects such concentrations can have on the physical and adhesive properties of the adhesive. The device also overcomes the shortcomings associated with oral or buccal nicotine dosage forms, such as the indigestion or jaw soreness associated with nicotine chewing gum.

SUMMARY OF THE INVENTION

It is accordingly an object of this invention to provide a rate controlled transdermal nicotine delivery device having an in-line adhesive and a subsaturated nicotine reservoir, which device exhibits improved delivery rate characteristics.

Another object of this invention is to provide a device which overcomes incompatibility problems between the nicotine and other components of a transdermal delivery device which are associated with high nicotine activity.

It is a further object of this invention to provide a transdermal delivery device capable of delivering nicotine base to the systemic circulation at levels sufficient to reduce the urge to smoke.

It is a further object of this invention to minimize the residual nicotine in the device after use.

These and other objects have been achieved by the present invention wherein a rate controlled, subsaturated transdermal nicotine delivery device having an in-line adhesive utilizes a subsaturated reservoir, preferably at a thermodynamic activity no greater than about 0.5, containing an amount of nicotine sufficient to prevent the activity from decreasing by more than about 75% and preferably less than about 25% during the predetermined delivery period. The device is also typically designed such that no more than, and preferably substantially less than, half of the total nicotine loading is in the adhesive and rate controlling membrane layers after equilibration and prior to use.

BRIEF DESCRIPTION OF THE DRAWINGS

The invention will be described in further detail with reference to the accompanying drawings wherein.

DESCRIPTION OF THE INVENTION

Figure 1:
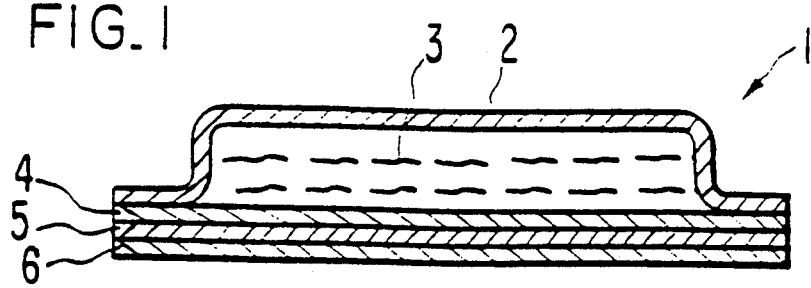
FIG. 1 is a cross-sectional view of an embodiment of the transdermal delivery devices according to this invention.
Figure 2:
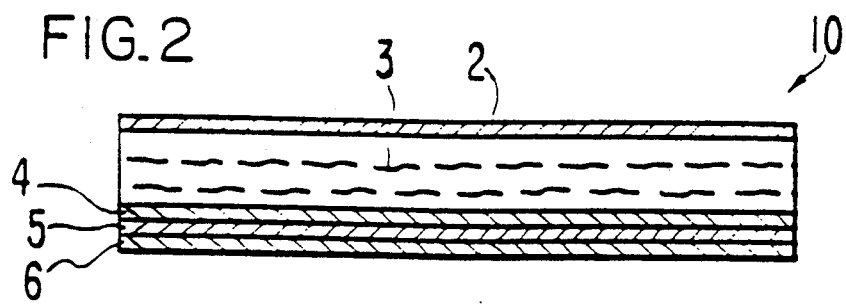
FIG. 2 is a cross-sectional view of another embodiment of the transdermal delivery devices according to this invention.

Referring now to FIGS. 1 and 2 (like reference numerals referring to common elements), transdermal delivery devices 1 and 10 according to this invention are shown. Devices 1 and 10 are formed of an impermeable backing 2, a subsaturated nicotine reservoir 3, a nicotine release rate controlling membrane 4, and an in-line contact adhesive 5 permeable to the passage of nicotine. A strippable release liner 6 is also included and is adapted to be removed from the adhesive layer prior to application to the skin of the subject to whom the nicotine is to be administered.

The embodiments of FIGS. 1 and 2 differ in that in FIG. 1 the impermeable backing 2 is heat sealed at its periphery to the rate controlling membrane 4 to form a pouch fully enclosing reservoir 3 to prevent it from flowing or oozing. In the embodiment of FIG. 2 the reservoir 3 has sufficient viscosity to maintain its structural integrity without a peripheral or circumferential seal. In both embodiments, nicotine is present in the reservoir 3 in an amount below the saturation concentration. Arrangements of the adhesive, reservoir and rate controlling means, other than those of FIGS. 1 or 2, are usable according to this invention. For example, an adhesive having microcapsules dispersed therethrough as shown in aforementioned U.S. Pat. No. 3,598,123, said microcapsules containing nicotine at a thermodynamic activity less than 1.

The transdermal delivery devices, according to this invention, are intended to be applied to a patient for a predetermined administration period, which typically would be from about 8 hours up to several days, and preferably 24 hours for ease in patient compliance. During the administration period it is preferred to control the amount of nicotine that is released from the device so that the nicotine can be administered to the patient in a predetermined and controlled manner.

The in vitro nicotine release rate or flux from a transdermal delivery device according to this invention directly into an infinite sink as a function of time can be considered to consist of two phases, a first, initial "transient" phase, and a second, subsequent "steady-state" delivery phase. During the initial transient phase, the nicotine is released at a high rate as a result of the initial loading of nicotine in the adhesive and rate controlling membrane layers, 5 and 4, respectively. This initial pulse decreases relatively rapidly until the initial loading of nicotine in the adhesive layer is depleted and the "steady-state" phase in which nicotine is being delivered from reservoir 3 through rate controlling membrane 5 commences.

Figure 3:
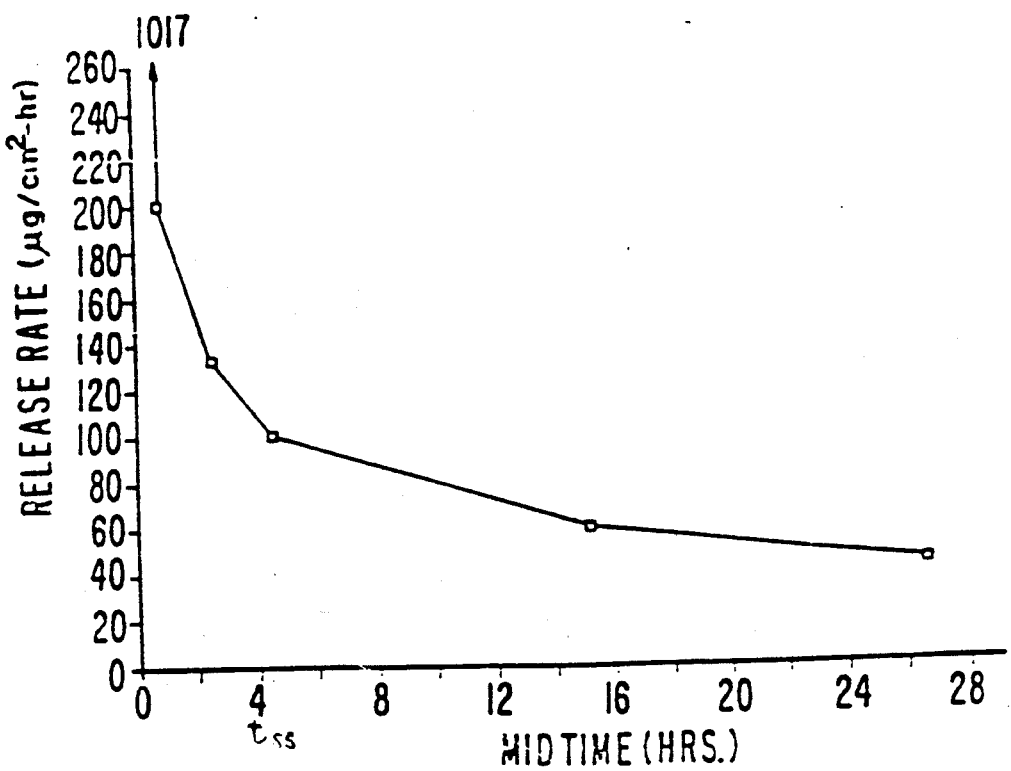
FIG. 3 contains a plot of the in vitro release rates at 35° C. vs. time, for embodiments of this invention.

FIG. 3 illustrates the in vitro release rate of subsaturated nicotine systems according to this invention. The data points on the time line represent the midtime between sampling points. Thus, the average release rate is measured between $t_1$ and $t_2$, and is plotted at midtime $t_i$, where $t_i$ is midway between $t_1$ and $t_2$. The $t_{ss}$ position indicated on FIG. 3, represents the approximate time at which the initial transient phase ends and the steady state delivery phase commences.

The variation of release rate with time during the steady-state phase depends on the structure of the device. For example, simple monoliths of the prior art exhibit a theoretical variation of steady-state release rate as a function of $t^{-\frac{1}{2}}$, whereas prior art devices having unit activity reservoirs and release rate controlling membranes exhibit theoretical steady-state release rates that vary with $t^0$, i.e., they remain constant. Devices according to this invention exhibit a theoretical release rate which varies as a function of $t^n$, where n is greater than $-\frac{1}{2}$ and less than 0. Preferred embodiments exhibit in vitro release rates which approach those obtained from zero order devices, i.e., the value of n is closer to 0 than to $-\frac{1}{2}$.

According to the preferred embodiments of this invention, the steady-state in vitro release rate can be maintained substantially constant from the termination of the initial transient phase until the expiration of the predetermined administration period. As used herein, the in vitro nicotine delivery rate is considered to be "substantially constant" if the steady-state rate does not vary more than about ±50%, and preferably no more than ±25%, during the steady-state administration period.

The maximum allowable concentration of nicotine in the adhesive will be determined by such factors as the nicotine concentration at which the adhesive properties may be impaired, the nicotine concentration at which irritation problems or unacceptably high initial transdermal nicotine fluxes, for example, are observed. When such undesirable effects occur, the initial activity of nicotine in the adhesive should preferably be at a lower level. Because the device will equilibrate upon standing, the activity (but not necessarily the concentration) of nicotine in the reservoir will ultimately be the same as the activity of nicotine in the adhesive layer.

Transdermal devices for the delivery of nicotine according to our invention have the following characteristics:

1. The device utilizes an in-line adhesive to maintain the device on the skin;

2. The initial equilibrated concentration of the nicotine in the reservoir 3 and the adhesive 5 is below saturation, expressed alternatively, the thermodynamic activity is less than 1.0 and preferably in the range of about 0.05–0.50; and most preferably in the range of 0.20–0.40.
3. The reservoir 3 comprises the nicotine dissolved in a solvent with respect to which the rate controlling means 4 is preferably substantially impermeable;
4. In preferred embodiments the initial loading of the nicotine in reservoir 3 is sufficient to prevent the activity of the nicotine in the reservoir from decreasing by more than about 75% and preferably no more than about 25% during the predetermined period of administration; and
5. In preferred embodiments the thicknesses of the adhesive, rate controlling membrane and reservoir layers are selected so that at least 50% and, preferably at least 75% of the initial equilibrated nicotine loading is in the reservoir layer.

Studies with nicotine releasing gum (Nicorette ®), have determined that the target blood level of nicotine for reducing the urge to smoke is approximately 12–15 nanograms/ml and that the clearance of nicotine from the body occurs at about 18 ml/min-kg. An estimate of the target transdermal administration rate can be made from this data.

A 70 kg person, for example, would have a target input rate of:

(70 kg) (18 ml/min-kg) (60 min/hr) (0.012 $\mu$g/ml) = 907 $\mu$g/hr For a 20 cm$^2$ transdermal system, the average target flux would be:

(907 $\mu$g/hr)/(20 cm$^2$) = 45 $\mu$g/cm$^2$-hr

These calculations are merely illustrative of the invention and are not meant to be limiting in any manner.

To account for individual variability, target steady-state in vivo administration rates within the range of about 250–4000 $\mu$g/hr with a typical average rate being about 1000 $\mu$g/hr are contemplated. The flux of nicotine through skin varies somewhat from individual to individual and from body site to body site but generally appears to be in the range of about 400–950 $\mu$g/cm$^2$ hr. Accordingly the preferred administration rates can be readily achieved according to our invention in a rate controlled device having a size in the range of about 5–50 cm$^2$. A one day delivery period can readily be obtained from subsaturated devices of this invention, and administration periods of about 8–10 hours and up to about 3 days can be attained by varying the thickness of the reservoir.

Although administration periods of 24 hours appear preferable from clinical studies and have the advantage of application and removal of the device occurring simultaneously at the same time each day, other administration periods, such as about 16 hours, have also proved effective. A simple manner of achieving 16 hour administration is to apply the device each day upon waking, wear it all day, and remove and discard just prior to sleep. This pattern would be repeated for as long as nicotine therapy is desired.

Total nicotine loading in a transdermal delivery device of this invention is preferably at least about 50 mg with the equilibrated concentration of nicotine in the reservoir composition being within the range of 5–50 wt %, corresponding to an activity within the range of 0.05–0.50 if the nicotine is miscible with the reservoir composition.

Reaction of the skin to nicotine is flux dependent and to minimize skin reaction it is preferred to maintain the average transdermal flux, particularly with the longer administration periods of about 16 hours or more, below about 200 $\mu$g/cm$^2$-hr and preferably to maintain the steady state transdermal flux below about 120 $\mu$g/cm$^2$.hr. Typically, the steady-state flux will be in the range of about 30 to 70 $\mu$g/cm$^2$-hr.

The equilibrated nicotine loading in the reservoir layer is preferably selected to be sufficient to enable the total dose of nicotine delivered during the predetermined administration period to be delivered while maintaining the decrease in activity of the nicotine in the reservoir within the limits noted above. The total loading of nicotine in each layer of the device can be readily varied without changing the activity, simply by increasing or decreasing the volume of the adhesive, rate controlling means and/or reservoir means also by appropriate selection of the total surface area of the device through which nicotine is delivered. Because the rate controlling means can only act as a release rate limiting element on the nicotine which is in the reservoir, the reservoir volume or thickness should be selected with respect to the thicknesses of the rate controlling means and the adhesive, such that at least half, and preferably substantially more, of the initial equilibrated nicotine loading is in the reservoir.

Various materials suited for the fabrication of the various components are disclosed in the aforementioned patents. The matrix of reservoir 3 is preferably anhydrous and suitable materials include, without limitation, natural and synthetic rubbers or other polymeric materials, thickened mineral oils or silicone fluids or petroleum jelly. The preferred embodiment according to this invention is fabricated from an ethylene vinyl acetate (EVA) copolymer of the type described in U.S. Pat. No. 4,144,317, preferably having a vinyl acetate (VA) content within the range of about 28–60 weight percent.

The reservoir may also include dyes, pigments, inert fillers, diluents, antioxidants, antibacterials, stabilizers, vehicles, anesthetics, rubefacients, antipruritics, gelling agents and other conventional components of pharmaceutical products or transdermal therapeutic systems, as are well known in the art.

The rate controlling membrane 5 may be of a dense polymer film that has the requisite permeability to nicotine. The membrane material would be selected such that the flux of the nicotine through the membrane directly into a sink is preferably no greater than the in vitro flux of nicotine across skin (which would produce about 50% system control) and preferably substantially less.

The fractional control of nicotine, $J_{net}/J_{device}$, delivered across skin from the rate controlled transdermal therapeutic system of this invention may be determined from the following relationships where $J_{net}$ is the transdermal nicotine flux from the device, $J_{device}$ is the in Vitro release rate of nicotine from the device directly into a sink and $J_{skin}$ is the permeability of the skin to nicotine:

$$J_{net}/J_{device} = [(J_{device}/J_{skin}) + 1]^{-1}$$

Thus, if the $J_{skin}$, which is typically in the range of 400–950 $\mu$g/cm$^2$ hr., is greater than $J_{device}$ by a factor of about 2.4, i.e., $J_{device}$ is in the range of about 170–395, the fractional control of nicotine flux from the system would be:

$$J_{net}/J_{device} = [(1/2.4)+1]^{-1} = 0.7$$

Therefore, approximately 70% of the rate control is obtained from the system, and $J_{net}$ would be in the range of about 115–280. Because of the high permeability of skin and the low net flux required, system control in the range of 95–98% can be readily achieved according to this invention.

Preferably the rate controlling membrane 4 is substantially impermeable to the component of reservoir 3 in which the nicotine is dissolved. However, this invention also contemplates use of a rate controlling membrane that is permeable to the passage of components of the reservoir such as anesthetics, rubefacients, permeation enhancers, and antipruritics for example.

Examples of the types of polymer films that may be used to make the membrane 16 are disclosed in U.S. Pat. Nos. 3,797,494 and 4,031,894, both of which are incorporated herein by reference. Particularly suitable materials are low density polyethylene, high density polyethylene and ethylene vinyl acetate copolymers.

The composition and thickness of adhesive layer 5 is selected such that the adhesive does not constitute a significant permeation barrier to the passage of nicotine and is compatible with nicotine at the activity chosen for the device. Numerous adhesives are known to the art for use as transdermal in-line adhesives. Suitable adhesive materials are listed in the aforementioned patents, a preferred adhesive being a polyisobutylene adhesive of the type described in the aforementioned application of Wang, et al. Amine resistant adhesives, such as silicone adhesives which may be modified with silicone oil to obtain the desired tack, are also useful in this invention.

The backing member 2 serves the purposes of preventing passage of the drug or environmental moisture through the surface of the reservoir distant from the skin, and also for providing support for the system, where needed. The backing layer is impermeable to the passage of nicotine and can be flexible or nonflexible. Suitable materials include, without limitation, polyethylene terephthalate, some types of nylon, polypropylene, metallized polyester films, polyvinylidene chloride and aluminum foil.

Having thus generally described our invention, the following description and Examples will illustrate and describe various embodiments of our invention.

EXAMPLE I

Transdermal delivery devices for the controlled delivery of nicotine were prepared utilizing a highly permeable, amine resistant silicone adhesive available from Dow Corning (X7-2920), low density polyethylene (LDPE) as the rate controlling membrane, EVA (40% VA) as the non-diffusible drug reservoir diluent, pigmented medium density polyethylene/aluminized polyester as the impermeable backing member and nicotine base as the source of nicotine. Nicotine is extremely soluble (essentially miscible) in the EVA (40% VA) diluent and thus the weight percent concentration in the diluent corresponds approximately to the thermodynamic activity. The devices tested had 4 mil (0.1 mm) LDPE rate controlling membranes, and 6 mil (0.15 mm) drug reservoirs containing either 20 or 25 weight percent nicotine base. The adhesive layer was cast to a dry thickness of 2 mils (0.05 mm). In vitro skin flux data for these devices are shown in Table I. The nicotine flux data across skin was obtained from averaging the data generated by systems tested on two different skin donors.

TABLE I

| Time (hr) | Drug Flux with 20 wt % drug ($\mu$g/cm2 − hr) | Drug Flux with 25 wt % drug ($\mu$g/cm2 − hr) |
| --- | --- | --- |
| 2 | 87.9 | 133.2 |
| 4 | 65.8$t_{ss}$ | 104.6$t_{ss}$ |
| 6 | 52.6 | 85.0 |
| 8 | 47.5 | 73.2 |
| 23.25 | 33.4 | 52.8 |
| 27.25 | 27.9 | 45.2 |
| 30.75 | 23.1 | 40.3 |

Thicker rate controlling and adhesive layers would provide a higher initial pulse as compared to thinner layers which would provide a smaller initial pulse for the same initial activity. $t_{ss}$ indicates the approximate time of commencement of the steady state.

EXAMPLE II

Nicotine transdermal delivery devices 1 cm$^2$ were fabricated comprising a 30 wt % nicotine/70 wt % EVA 40 reservoir composition (0.30 nicotine activity), a 2 mil (0.05 mm) high density polyethylene (HDPE) rate controlling membrane and a 2 mil (0.05) amine resistant silicone adhesive layer (Dow Corning X7-2920 with 5 wt % silicone fluid). The in vitro release rate at 35° C. is shown in FIG. 3. A system at least 10 cm$^2$ in size, designed according to the embodiment of Example II and having a 50 mg or 5 mg/cm$^2$ drug loading, should deliver nicotine at an average 24 hour administration rate of about 1000 $\mu$g/hr. when applied to human subjects on a daily basis.

EXAMPLE III

Subsaturated systems according to this invention were fabricated comprising a nicotine/EVA 40 reservoir, a 4 mil (0.10 mm) LDPE rate controlling membrane and an amine resistant in-line adhesive. Systems having varying nicotine activities up to 0.40 were tested on rabbits and guinea pigs and systems having activities of up to 0.40 were tested on humans. These systems were only minimally irritating. We believe that high flux rates associated with systems having high (greater than 0.50) or unit activity may cause irritation. This is evidenced by the fact that of the systems tested on humans, irritation, while still minimal, appeared to increase with increasing activity.

EXAMPLE IV

Subsaturated transdermal nicotine delivery devices were made by extruding a 0.13 mm thick drug reservoir film comprising a subsaturated solution of 40% nicotine base in 60% EVA (40% VA) between an impermeable, pigmented aluminized polymer backing (Medpar TM) and a high density polyethylene (HDPE) rate-controlling membrane 0.05 mm thick. This trilaminate was laminated to adhesives consisting of blends of low molecular weight (35K) polyisobutylene (LMW PIB) and high molecular weight (1.2M) polyisobutylene (HMW PIB) in weight ratios of LMW:HMW of 80:20, 85:15 and 90:10, that were solvent cast to a thickness of 0.05 mm from n-heptane solution onto a 0.076 mm strippable release liner formed of fluorocarbon diacrylate/- polyethylene terephthalate (PET), (3M 1022) or siliconized PET and allowed to reach equilibrium. All samples exhibited good adhesive properties and had 24 hour average in vitro release rates ($J_{device}$) into water at 37° C. of 60 μg/cm² hr, 70 μg/cm² hr, and 72 μg/cm² hr respectively.

EXAMPLE V

Devices were fabricated according to the procedures of Example IV using PIB adhesive blends of LMW:HMW of 75:25 and 80:20 and substituting, as the drug reservoir, a mixture of 70 wt % EVA-40 and 30 wt % nicotine base. The weight percent of the nicotine in the adhesives upon equilibration was found to be about 11 weight percent. Devices were fabricated according to the procedures of Example IV, using a PIB adhesive of Formula B, and reservoir compositions of 20%, 30% and 40% nicotine base in EVA-40. The weight percent of nicotine in the PIB adhesive after equilibration was found to be as follows: 8 wt. percent in the 20% nicotine reservoir device; 10 wt. percent in the 30% nicotine reservoir device; and 14 wt. percent in the 40% nicotine reservoir device.

EXAMPLE VI

The devices had an initial nicotine loading of 5.2 mg/cm² for a total loading of 78 mg. After 24 hours the nominal residual nicotine loading was 54 mg corresponding to a decrease in activity of approximately 52%.

Transdermal nicotine delivery devices fabricated as set forth in Example IV were cut into fifteen square centimeter devices, using LMW:HMW PIB adhesive blends of 90:10 and 85:15 having a nominal average administration rate of about 1 mg/hr.

These devices were used in clinical studies to evaluate their safety and efficacy as an aid to the withdrawal of smoking in healthy adult cigarette smokers, motivated to stop smoking. The devices were compared to placebos in blind studies for periods of four weeks in a pilot study and six weeks in a definitive study in different treatment regimes involving (a) application upon waking in the morning with removal and reapplication 24 hours later and (b) application upon waking and removal at bedtime, approximately 16 hours thereafter, followed by reapplication in the morning.

Safety was evaluated by noting any reactions that may have occurred during the study and efficacy was evaluated by determining the number and percentage of patients who smoked no cigarettes during the last two weeks of the pilot study and the last four weeks of the definitive study as ascertained by patient questionnaires and corroborated by measurement of expired carbon monoxide at levels of less than or equal to 8 parts per million. Morning craving for cigarettes, incidents of insomnia and severity of withdrawal symptoms were also assessed. A follow-up after approximately 6 months on those patients who smoked no cigarettes during the last two weeks of the study was also made.

Based on the results of these studies it appears that the transdermal nicotine in both 16 and 24 hour regimes was more effective, as compared to the placebo, in both short term and long term smoking cessation and that the incidence of serious skin reaction was low. In a sensitization study using 2.5 cm² test samples formed from the formulation using the 90:10 adhesive blend described above only 3 out of 186 participants became sensitized.

Having thus generally described our invention and preferred embodiments thereof, it is apparent that various modifications and substitutions will be apparent to workers skilled in the art. These modifications and substitutions can be made without departing from the scope of our invention which is limited only by the following claims.

We claim:

1. A medical device for the transdermal administration of nicotine, said device being adapted to deliver nicotine during a predetermined nicotine administration period of at least about eight hours at a rate within the range of about 250–4000 μg/hr for a substantial portion of said administration period, said device comprising, in combination:
   a. nicotine reservoir comprising said nicotine dissolved in a solvent at a concentration less than saturation and at an initial equilibrated nicotine loading sufficient to prevent the concentration of nicotine in said solvent from decreasing by more than 75% during said administration period;
   b. nicotine release rate controlling means disposed in the path of nicotine migration from said reservoir to the skin, said rate controlling means being permeable to nicotine and substantially impermeable to said solvent;
   c. adhesive means disposed in the path of nicotine migration from said release rate controlling means to the skin; and
   d. removable release liner means on said adhesive.

2. The device of claim 1 wherein the initial equalibrated thermodynamic activity of nicotine is no greater than about 0.50.

3. The device of claim 2 wherein said adhesive has a high nicotine solubility.

4. The device of claim 2 wherein at least 50% of the initial loading of the nicotine in the device is in the nicotine reservoir.

5. The device of claim 2 wherein said decrease in activity is no greater than about 25%.

6. The device of claim 5, wherein at least 75% of the initial nicotine loading is in the reservoir.

7. The device of claim 2 wherein said rate controlling means is substantially impermeable to the passage of the reservoir solvent.

8. The device of claim 1 wherein the initial equilibrated thermodynamic activity of nicotine in said reservoir and adhesive layers is in the range of about 0.20–0.40.

9. A medical device for the transdermal administration of nicotine utilizing an in-line adhesive, said device being adapted to deliver nicotine at a rate within the range of about 250–4000 μg/hr during a substantial portion of a predetermined administration period of at least about 8 hours comprising, in combination:
   a. a nicotine reservoir comprising nicotine dissolved in an ethylene vinyl acetate copolymer at a concentration less than saturation and at an initial equilibrated nicotine loading sufficient to prevent the thermodynamic activity of nicotine in said ethylene vinyl acetate copolymer from decreasing by more than 75% during said administration period;
   b. nicotine release rate controlling means disposed in the path of nicotine migration from said reservoir to the skin said rate controlling means being permeable to nicotine and substantially impermeable to said solvent and being selected form the group consisting of low density polyethylene, high density polyethylene and ethylene vinyl acetate copolymers;
c. adhesive means disposed in the path of nicotine migration from said release rate controlling means to the skin; and
d. removable release liner means on said adhesive.

10. The device of claim 9 wherein the initial equilibrated thermodynamic activity of nicotine is no greater than about 0.50.

11. The device of claim 10 wherein the thickness of said reservoir, rate-controlling and adhesive means are selected such that at least 50% of the initial equilibrated loading of nicotine is in the reservoir.

12. The device of claim 10 wherein the thickness of said reservoir, rate-controlling and adhesive means are selected such that at least 75% of the initial equilibrated loading of nicotine is in the reservoir.

13. The device of claim 11 wherein the initial equilibrated loading of nicotine in said reservoir is sufficient to prevent the thermodynamic activity of said nicotine in said solvent from decreasing by more than 25% during said administration period.

14. The device of claim 12 wherein the initial equilibrated loading of nicotine in said reservoir is sufficient to prevent the thermodynamic activity of said nicotine in said solvent from decreasing by more than 25% during said administration period.

15. The device of claim 9 wherein the initial equilibrated thermodynamic activity of nicotine in said reservoir and adhesive layers is in the range of about 0.20–0.40.

16. The device of claim 14 wherein the initial equilibrated thermodynamic activity of nicotine in said reservoir and adhesive layers is in the range of about 0.20–0.40.

17. The device of claim 16 wherein said ethylene vinyl acetate reservoir copolymer has a vinyl acetate content of about 40%.

18. A medical device for the transdermal administration of nicotine, said device comprising, in combination:
a. a subsaturated nicotine reservoir comprising 5 to 40 wt % nicotine and 60 to 95 wt % ethylene vinyl acetate copolymer having a vinyl acetate contact in the range of about 28–40%, said reservoir containing sufficient nicotine to administer nicotine at a rate within the range of about 250 to 4000 $\mu g/hr$ during a substantial portion of an administration period of at least about 8 hours while preventing the activity of said nicotine from decreasing by more than 75% during said administration period;
b. nicotine release rate controlling means disposed in the path of nicotine migration from said reservoir to the skin, said rate controlling means being a high density polyethylene membrane;
c. adhesive means disposed in the path of nicotine migration from said release rate controlling means to the skin: and
d. removable release liner means on said adhesive.

19. The device of claim 18 wherein said nicotine loading is about 5 $mg/cm^2$.

20. The device of claim 18 wherein the thickness of said reservoir, rate-controlling and adhesive means is selected such that at least 50% of the initial equilibrated nicotine loading is in the reservoir.

21. The device of claim 18 wherein said administration period is about 24 hours.

22. The device of claim 2 wherein the steady state flux is in the range of about 30–120 $\mu g/cm^2$ hr.

23. The device of claim 6 wherein the steady state flux is in the range of about 30–120 $\mu g/cm^2$ hr.

24. The device of claim 8 wherein the steady state flux is in the range of about 30–120 $\mu g/cm^2$ hr.

25. The device of claim 10 wherein the steady state flux is in the range of about 30–120 $\mu g/cm^2$ hr.

26. The device of claim 15 wherein the steady state flux is in the range of about 30–120 $\mu g/cm^2$ hr.

27. The device of claim 16 wherein the steady state flux is in the range of about 30–120 $\mu g/cm^2$ hr.

28. The device of claim 18 wherein the steady state flux is in the range of about 30–120 $\mu g/cm^2$ hr.

29. The device of claim 20 wherein the steady state flux is in the range of about 30–120 $\mu g/cm^2$ hr.

* * * * *